United States Patent
Wollenweber et al.

(12) United States Patent
(10) Patent No.: US 7,507,968 B2
(45) Date of Patent: Mar. 24, 2009

(54) SYSTEMS AND METHODS FOR CORRECTING A POSITRON EMISSION TOMOGRAPHY EMISSION IMAGE

(75) Inventors: Scott David Wollenweber, Waukesha, WI (US); Alexander Ganin, Whitefish Bay, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1421 days.

(21) Appl. No.: 10/462,914

(22) Filed: Jun. 17, 2003

(65) Prior Publication Data

US 2004/0260176 A1   Dec. 23, 2004

(51) Int. Cl.
*G01T 1/161* (2006.01)
*G01N 23/00* (2006.01)
*G06K 9/00* (2006.01)

(52) U.S. Cl. ............... 250/363.07; 250/363.09; 378/4; 378/19; 382/131

(58) Field of Classification Search ............... 250/252.1, 250/363.03, 363.04, 363.09; 382/131; 600/407, 600/425, 427, 436; 378/4, 19
See application file for complete search history.

(56) References Cited

U.S. PATENT DOCUMENTS

| | | | |
|---|---|---|---|
| 6,040,580 A | 3/2000 | Watson et al. | |
| 6,449,331 B1 | 9/2002 | Nutt et al. | |
| 6,462,342 B1 | 10/2002 | Stearns | |
| 6,490,476 B1 * | 12/2002 | Townsend et al. | 600/427 |
| 6,507,633 B1 | 1/2003 | Elbakri et al. | |
| 6,539,103 B1 | 3/2003 | Panin et al. | |
| 6,631,284 B2 * | 10/2003 | Nutt et al. | 600/427 |
| 2003/0004405 A1 | 1/2003 | Townsend et al. | |
| 2003/0190065 A1 * | 10/2003 | Hamill et al. | 382/131 |
| 2004/0101184 A1 * | 5/2004 | Sivaramakrishna et al. | 382/131 |
| 2004/0120565 A1 * | 6/2004 | Wollenweber | 382/131 |
| 2005/0129295 A1 * | 6/2005 | Shanmugam et al. | 382/131 |

OTHER PUBLICATIONS

Kinahan, P. E., D. W. Townsend, T. Beyer, and D. Sashin, 1998, "Attenuation Correction for a Combined 3D PET/CT Scanner", Med. Phys. 25 (10).*

* cited by examiner

*Primary Examiner*—David P Porta
*Assistant Examiner*—Casey Bryant
(74) *Attorney, Agent, or Firm*—The Small Patent Law Group; Dean D. Small

(57) ABSTRACT

A method for correcting a positron emission tomography (PET) emission image is described. The method includes obtaining a PET emission sinogram of an object, obtaining a computed tomography (CT) image for a scanned portion of the object, the object having a truncated portion outside a field of view (FOV) of a CT image, determining a correction set of CT data based on a measured set of CT data within the CT sinogram, generating modified attenuation correction factors from the measured and correction sets of CT data, and correcting the PET sinogram using the modified attenuation correction factors.

25 Claims, 18 Drawing Sheets

SYSTEMS AND METHODS FOR CORRECTING A POSITRON EMISSION TOMOGRAPHY EMISSION IMAGE

BACKGROUND OF THE INVENTION

This invention relates generally to imaging systems and more particularly to systems and methods for correcting a positron emission tomography (PET) emission image.

The systems and methods are directed toward multi-modal imaging systems capable of scanning using different modalities, such as, for example, but not limited to, Positron Emission Tomography (PET) and Computed Tomography (CT). The difference between multi-mode and multi-modality is that multi-mode systems are utilized to perform scans in different modes, for example, a flouro mode and a tomosynthesis mode, while a multi-modal system is utilized to perform scans in different modalities, for example, CT and PET. It is contemplated that the benefits of systems and methods for analyzing an abnormality of an, object accrue to all multi-modal imaging systems, such as, for example, but not limited to, a PET-CT imaging system.

PET has gained significant popularity in nuclear medicine because of the ability to non-invasively study physiological processes within a body of a patient. PET exhibits a high level of quantification accuracy, among nuclear medicine imaging instruments available. Applications requiring this accuracy include those in the fields of oncology, cardiology and neurology.

Using compounds such as $^{11}$C-labeled glucose, $^{18}$F-labeled glucose, $^{13}$N-labeled ammonia and $^{15}$O-labeled water, PET can be used to study such physiological phenomena as blood flow, tissue viability, and in vivo brain neuron activity. Positrons emitted by these neutron deficient compounds interact with free electrons in the body area of interest, resulting in the annihilation of the positron. This annihilation yields the simultaneous emission of a pair of photons approximately 180 degrees apart. A compound having the desired physiological effect is administered to the patient, and the radiation resulting from annihilation is detected by a PET tomography. After acquiring these annihilation "event pairs" for a period of time, the isotope distribution in a cross section of the body can be reconstructed.

PET data acquisition occurs by detection of both photons emitted from the annihilation of the positron in a coincidence scheme. Due to the approximate 180 degree angle of departure from the annihilation site, the location of the two detectors registering the "event" define a chord passing through the location of the annihilation. By histogramming these lines of response, a "sinogram" is produced that may be used by a process of back-projection to produce a three dimensional image of the activity. Detection of these lines of activity is performed by a coincidence detection scheme. A valid event line is registered if both photons of an annihilation are detected within a coincidence window of time. Coincidence detection methods ensure that an event line is histogrammed only if both photons originate from the same positron annihilation.

In CT, an external x-ray source is caused to be passed around the patient. Detectors around the patient then respond to x-ray transmission through the patient to produce an image of an area of study. Unlike PET, which are emission tomography techniques because they rely on detecting radiation emitted from the patient, CT is a transmission tomography technique which utilizes only a radiation source external to the patient.

BRIEF DESCRIPTION OF THE INVENTION

In one aspect, a method for correcting a positron emission tomography (PET) emission image is described. The method includes obtaining a PET emission sinogram of an object, obtaining a computed tomography (CT) image for a scanned portion of the object, the object having a truncated portion outside a field of view (FOV) of a CT image, determining a correction set of CT data based on a measured set of CT data within the CT sinogram, generating modified attenuation correction factors from the measured and correction sets of CT data, and correcting the PET sinogram using the modified attenuation correction factors.

In another aspect, a computer-readable medium encoded with a program is described. The program is configured to obtain a PET emission sinogram of an object, obtain a computed tomography (CT) image for a scanned portion of the object, the object having a truncated portion outside a field of view (FOV) of a CT image, determine a correction set of CT data based on a measured set of CT data within the CT sinogram, generate modified attenuation correction factors from the measured and correction sets of CT data, and correct the PET sinogram using the modified attenuation correction factors.

In yet another aspect, a method for correcting a positron emission tomography (PET) emission image is described. The method includes obtaining a computed tomography (CT) sinogram that is missing a portion of an object, creating a non-attenuation-corrected PET emission sinogram of the object, the PET emission sinogram being a histogram of PET emission data, determining a boundary of the object on the PET emission sinogram, comparing the boundary with a boundary of the object on the CT sinogram to determine the truncated portion, filling the portion with a first set of CT data located close to a portion of the boundary of the object on the CT sinogram, generating attenuation correction factors from a the first set and a second set of CT data located outside the portion, and correcting the PET emission data using the attenuation correction factors.

In still another aspect, an imaging system for correcting a positron emission tomography (PET) emission image is described. The imaging system includes a scanner having a plurality of detectors for acquiring a measured set of CT data and a controller operationally coupled to the scanner. The controller is configured to obtain a PET emission sinogram of an object, obtain a computed tomography (CT) image for a scanned portion of the object, the object having a truncated portion outside a field of view (FOV) of a CT image, determine a correction set of CT data based on a measured set of CT data within the CT sinogram, generate modified attenuation correction factors from the measured and correction sets of CT data, and correct the PET sinogram using the modified attenuation correction factors.

In another aspect, an imaging system for correcting an image is described. The imaging system includes a scanner having a plurality of detectors for acquiring a first dataset and a second dataset, the first dataset acquired from a first modality and the second dataset of data acquired from a second modality and a controller operationally coupled to the scanner. The controller is configured to obtain the first dataset of an object using the first modality, obtain the second dataset for a scanned portion of the object, the object having a truncated portion outside a field of view (FOV) of the second modality, determine a correction dataset based on the second dataset within the second modality, the second dataset being located proximate a boundary of the object on the second modality and being independent of data in the second dataset that is remote from the boundary, generate attenuation correction factors from the second and correction datasets, and correct the first dataset using the attenuation correction factors.

DETAILED DESCRIPTION OF THE INVENTION

Figure 1:
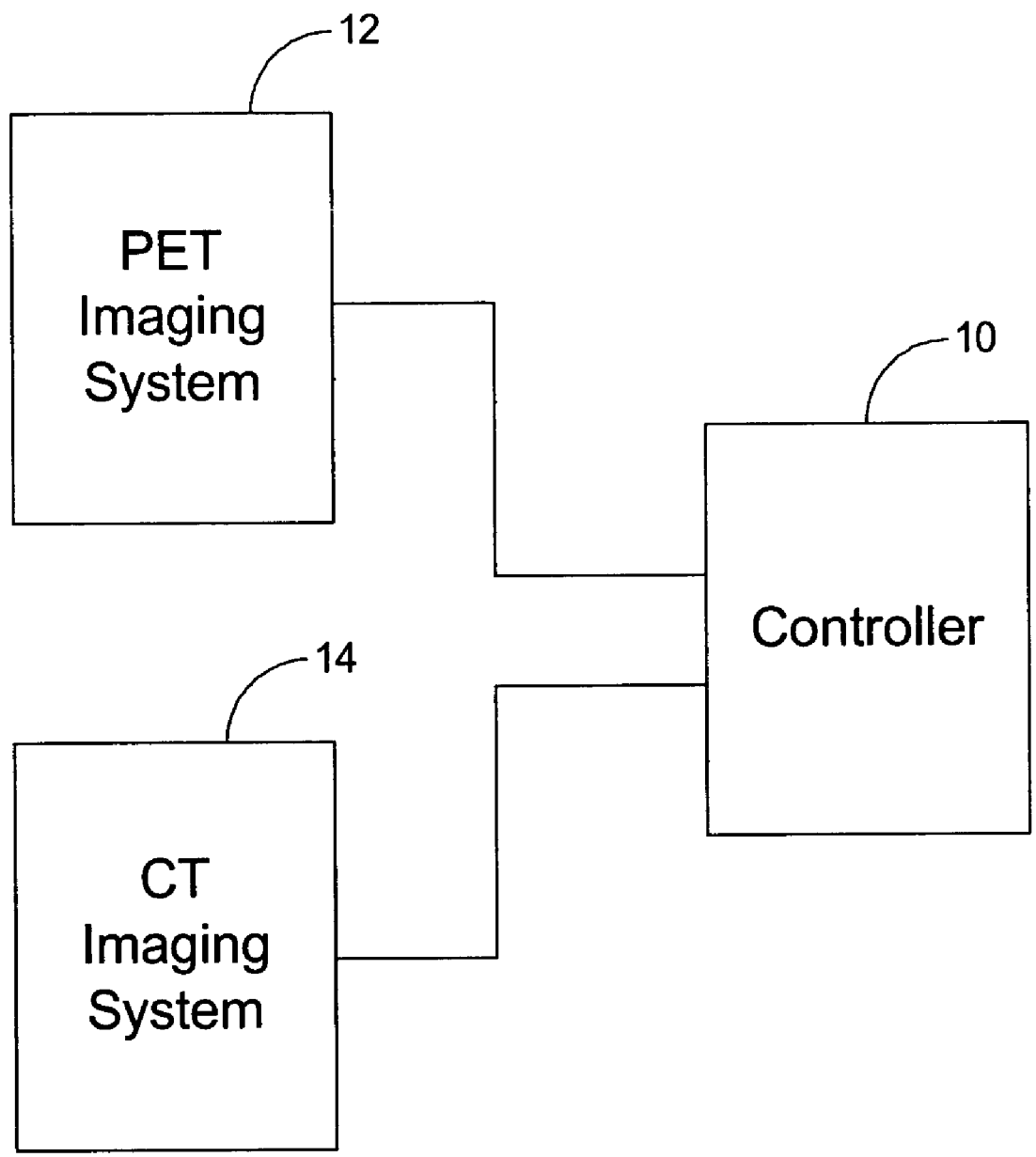
FIG. 1 is a block diagram of an embodiment of a system for correcting a positron emission tomography (PET) image.

FIG. 1 is a block diagram of an embodiment of a system for correcting a positron emission tomography (PET) image. System includes a controller 10 that is electrically coupled to a PET imaging system 12 and to a computed tomography (CT) imaging system 14. The term controller is not limited to just those integrated circuits referred to in the art as computers, but broadly refers processors, microcontrollers, microcomputers, programmable logic controllers, application specific integrated circuits, and other programmable circuits.

PET imaging system 12 constructs a PET emission image from PET emission data that is generated by positrons emitted from within an object, such as a patient or a phantom. The PET emission image is transmitted from PET imaging system 12 to controller 10. CT imaging system 14 creates a CT image from CT data that is produced as a result of attenuation of x-rays passing through the object. In order to achieve maximal quantitative measurement accuracy in the PET emission image, an attenuation correction must be applied to the PET emission data. In PET imaging system 12, this attenuation is dependent on both the total distance two gamma rays or photons must travel before striking a detector, and the density of attenuating media in the path of travel. Depending on the location of a line of response within the object's body, large variations in attenuating media cross section and density have to be traversed. If not corrected for, this attenuation causes unwanted spatial variations in the PET emission image that degrade the desired accuracy. As an example, for a cardiac study the attenuation is highest in the line of responses (LORS) passing through the width of torso and arms of the object, and attenuation is lowest in the LORs passing through from the front to the back of the chest of the object.

Attenuation correction factors (ACFs) that correct the attenuation are produced in a variety of ways. One of the methods includes using PET imaging system 12 to acquire transmission data by placing the object in a field of view (FOV) of PET imaging system 12 and rotating a positron-emitting source around the object, then acquire similar transmission data without placing the object in the FOV (i.e., "blank" scan), and finally calculate the ratios of the transmission data with the object in the FOV to the transmission data without the object in the FOV. Each of the ratios for a LOR is referred to as an ACF. Another method is to perform a CT scan with the object in a FOV of CT imaging system 14 to collect CT data. ACFs are obtained by converting the CT data acquired from the x-ray energy to the 511 keV PET energy using well-documented conversion methods. CT data that is acquired by placing the object in the FOV and performing a CT scan is used to form a CT sinogram, which is a histogram that shows number of events that are detected by each scintillator crystal of each detector of CT imaging system 14. The CT data is backprojected to obtain a CT image. Similarly, once PET emission data is corrected for attenuation, a PET emission image is produced, typically using a backprojection method.

Figure 2:
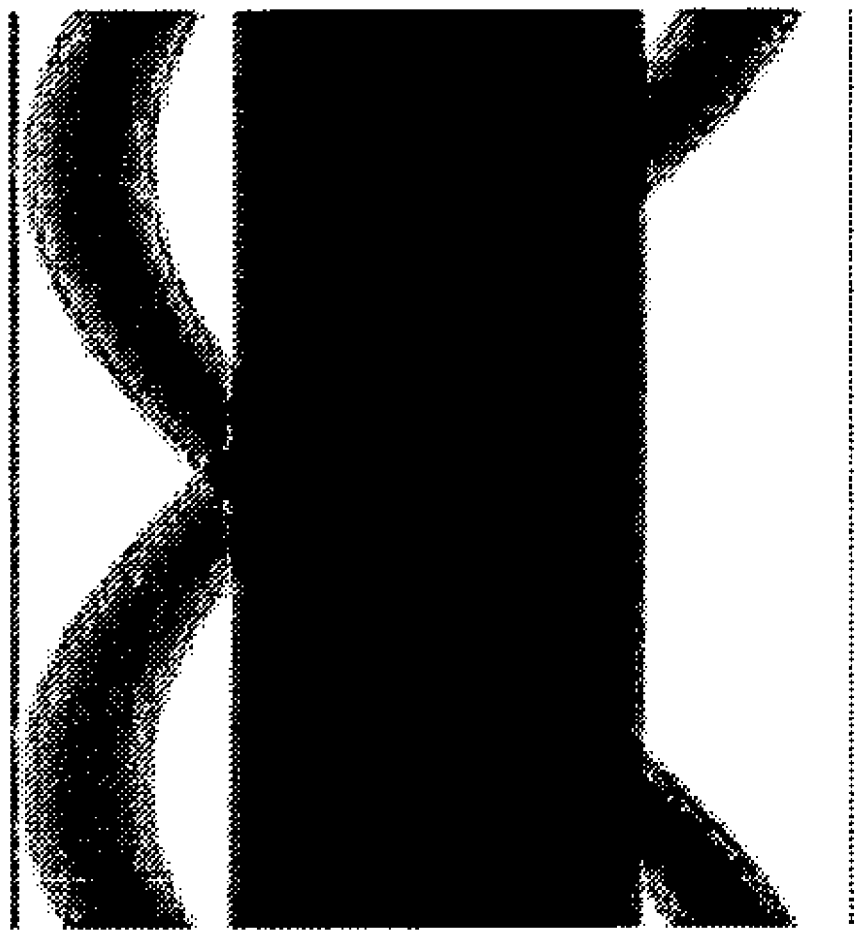
FIG. 2 is a PET transmission sinogram that is created by the system of FIG. 1.
Figure 3:
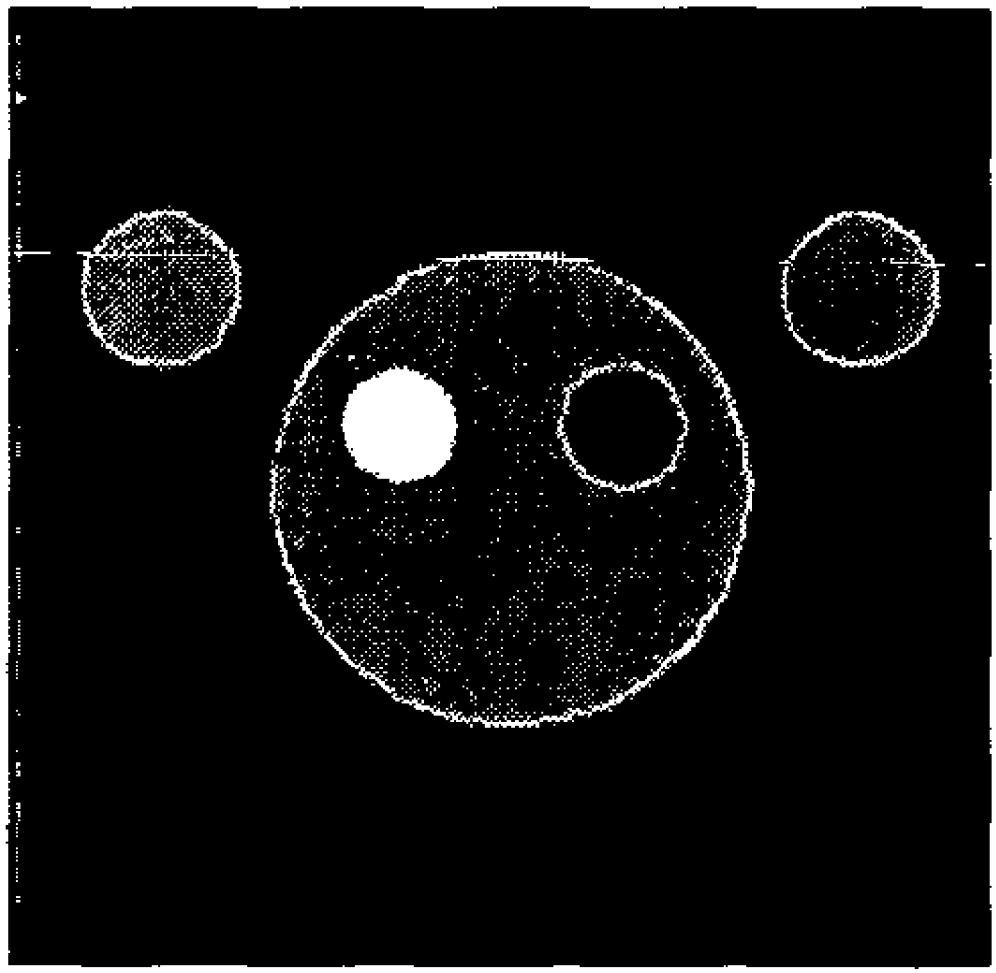
FIG. 3 is a reconstructed PET transmission image corresponding to the PET transmission sinogram data of FIG. 2.
Figure 4:
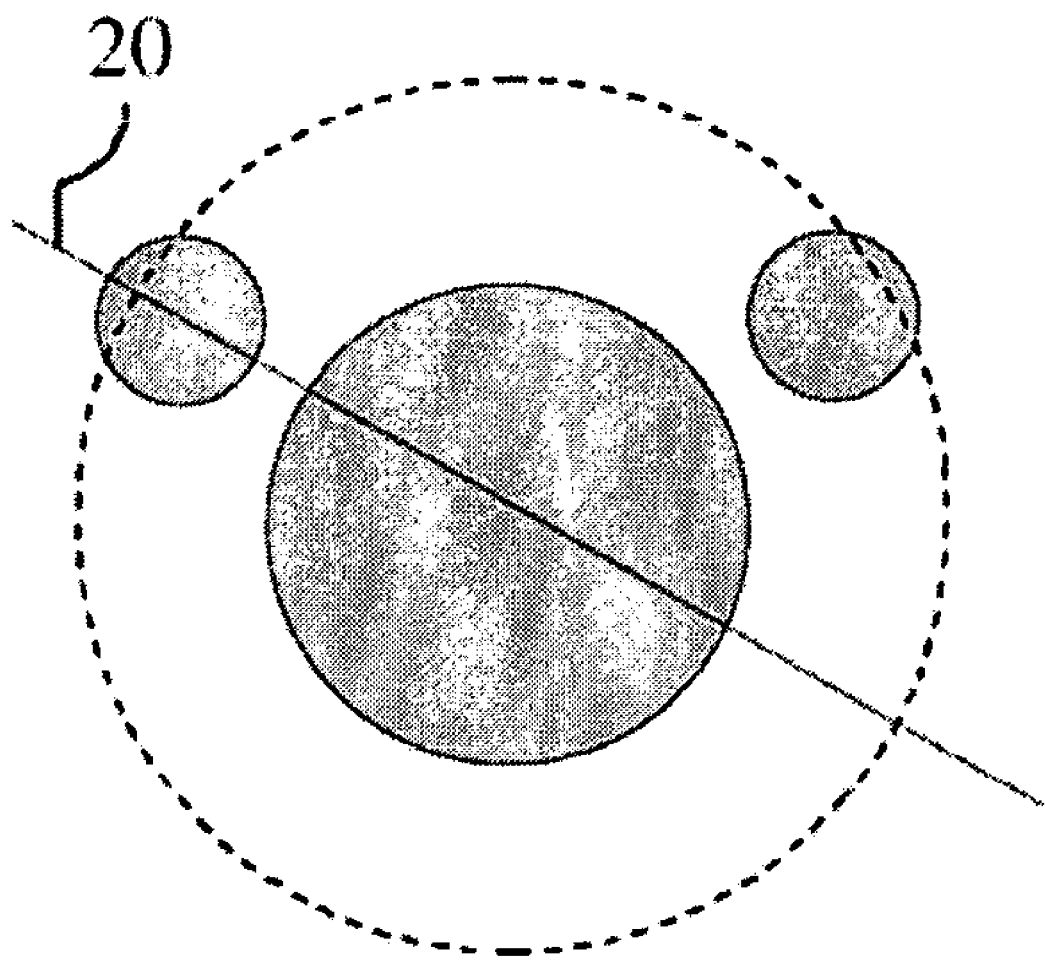
FIG. 4 shows a PET transmission image having a line along which transmission data is collected to correct for attenuation in PET emission data generated by the system of FIG. 1.

When performing a PET transmission scan using a PET imaging system 12, a FOV, such as, for instance, a diameter between 60 centimeters (cm) and 70 cm, of PET imaging system 12 is such that the object, including a portion, is within the FOV. The PET transmission scan results in a PET transmission sinogram, which is shown in FIG. 2, and can be used to produce a PET transmission image, which is shown in FIG. 3. The PET transmission sinogram includes information about the complete cross-section of the object. Transmission data is collected along a line 20, shown in FIG. 4, to generate ACFs that correct for attenuation along the complete LOR in the PET emission data. However, when performing a CT scan using CT imaging system 14, a FOV, such as, for instance, a 50 cm diameter, of CT imaging system 14 is such that a portion of the object that is scanned is outside the FOV.

Figure 5:
FIG. 5 is a CT sinogram that is created by the system of FIG. 1.
Figure 6:
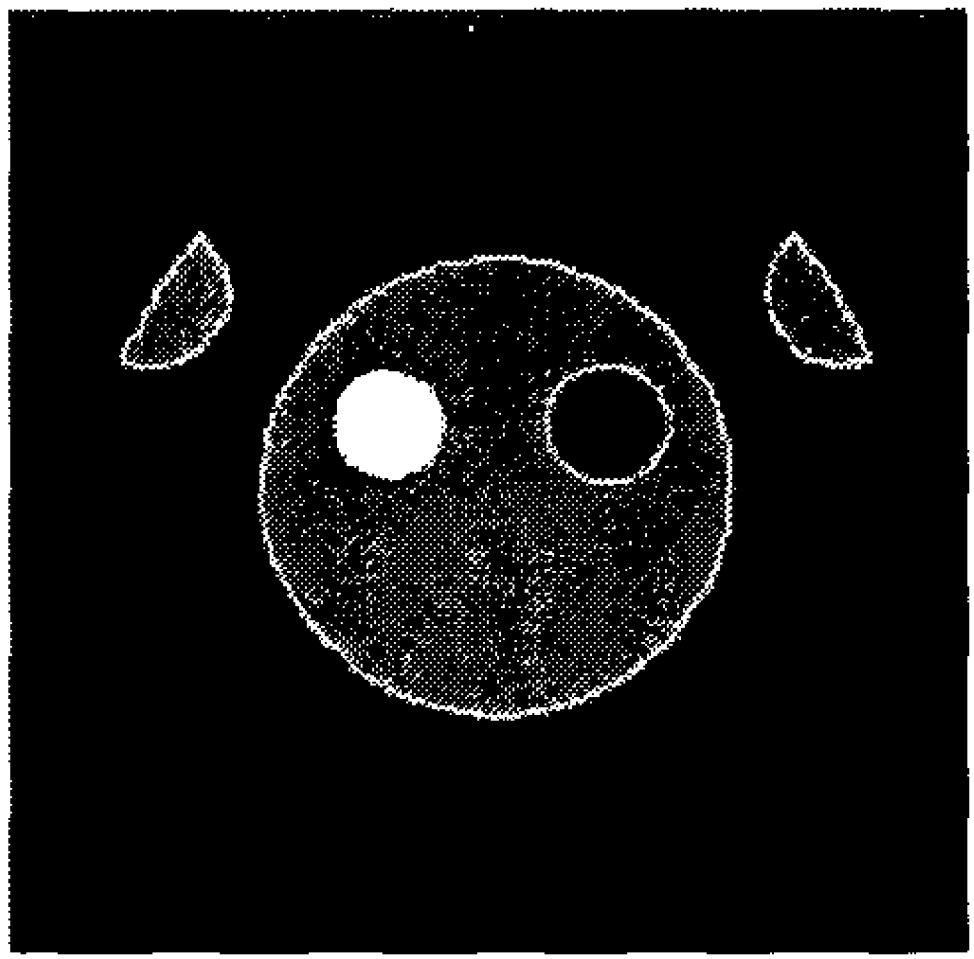
FIG. 6 is a reconstructed CT image that corresponds to the CT sinogram data of FIG. 5.
Figure 7:
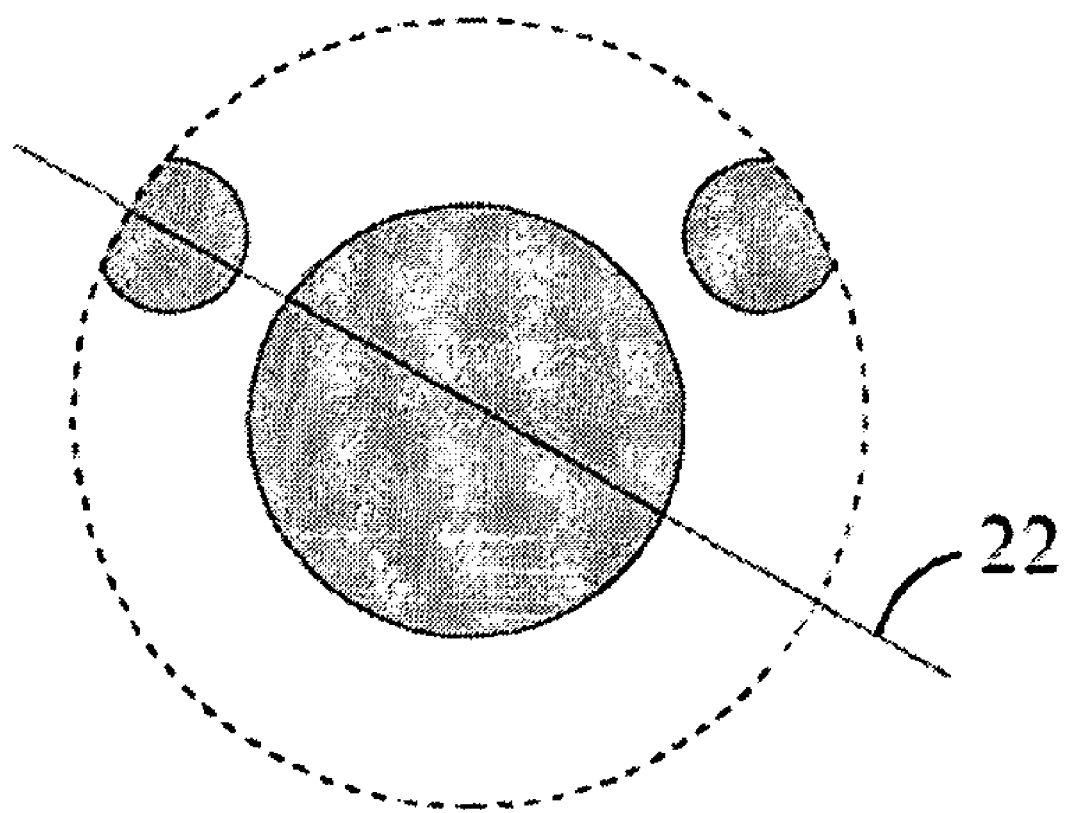
FIGS. 7 and 8 show CT images having lines along which CT data is collected to correct for attenuation in the PET emission data.
Figure 8:
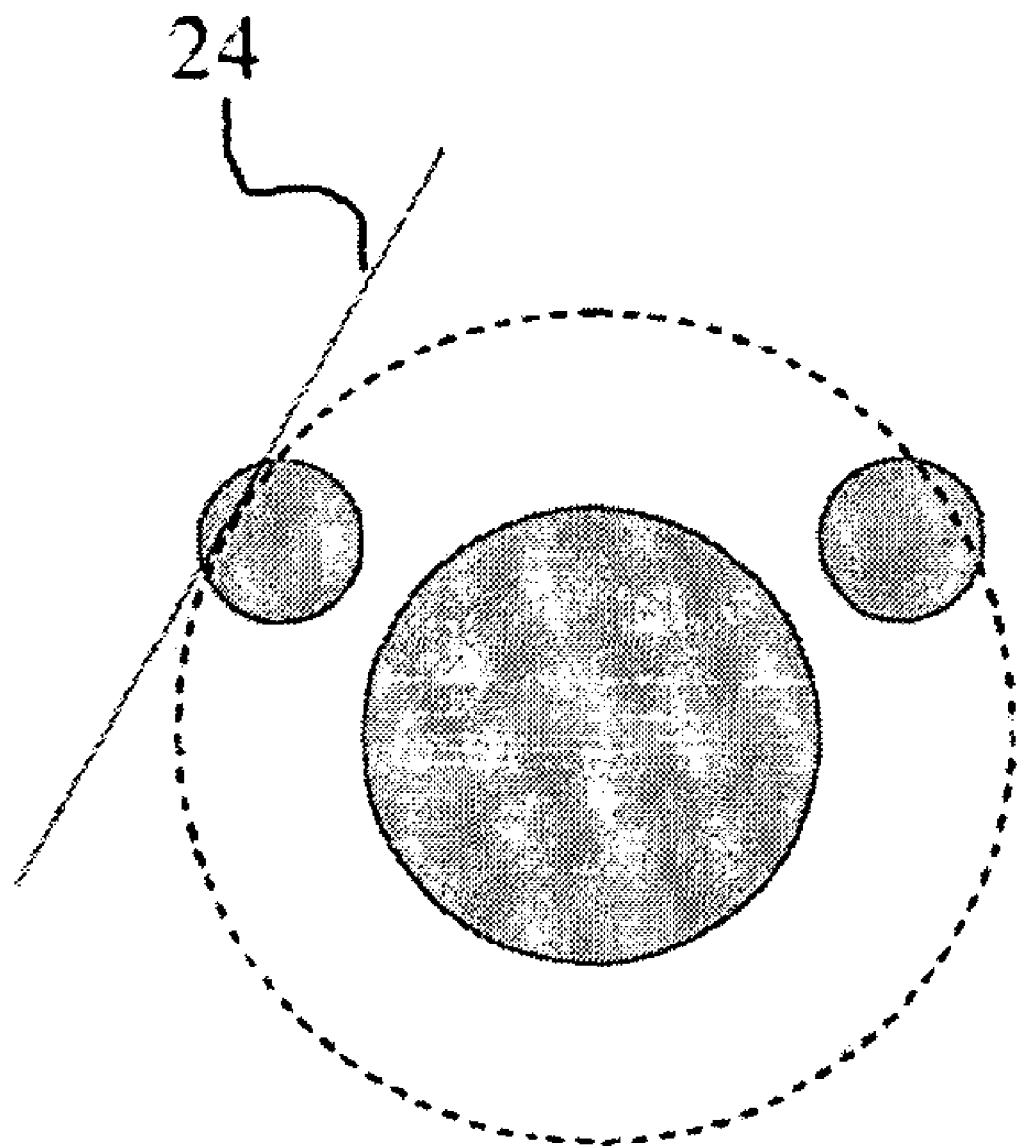
Figure 9:
FIG. 9 shows a PET emission image with artifacts that are generated due to using incomplete CT data for the purpose of attenuation correction.

CT sinogram, shown in FIG. 5, is produced via reprojection of a 50 cm diameter CT image, which is shown in FIG. 6. A CT scan therefore results in the CT sinogram and in the CT image. The CT sinogram does not include any information of portion of the object outside the FOV of CT imaging system 14 since it was formed from reprojection of the CT image of FIG. 6. CT data is collected along a line 22, shown in FIG. 7, or a line 24, shown in FIG. 8, to generate ACFs to correct for attenuation in PET emission data. However, since CT data corresponding to the portion is missing, the PET emission data corrected using these ACFs produces a PET emission image with artifacts and quantitative inaccuracies. An illustration of such a PET emission image with artifacts in arms of the object and near an upper left void of the object is shown in FIG. 9.

Controller 10 executes a method for correcting a PET emission image by using PET emission data that is not corrected for attenuation to find a boundary encompassing the portion of the object that is missing, filling the portion with CT data that is near the boundary, correcting the PET emission data with ACFs that are generated from collecting CT data within the boundary of the object.

Figure 10:
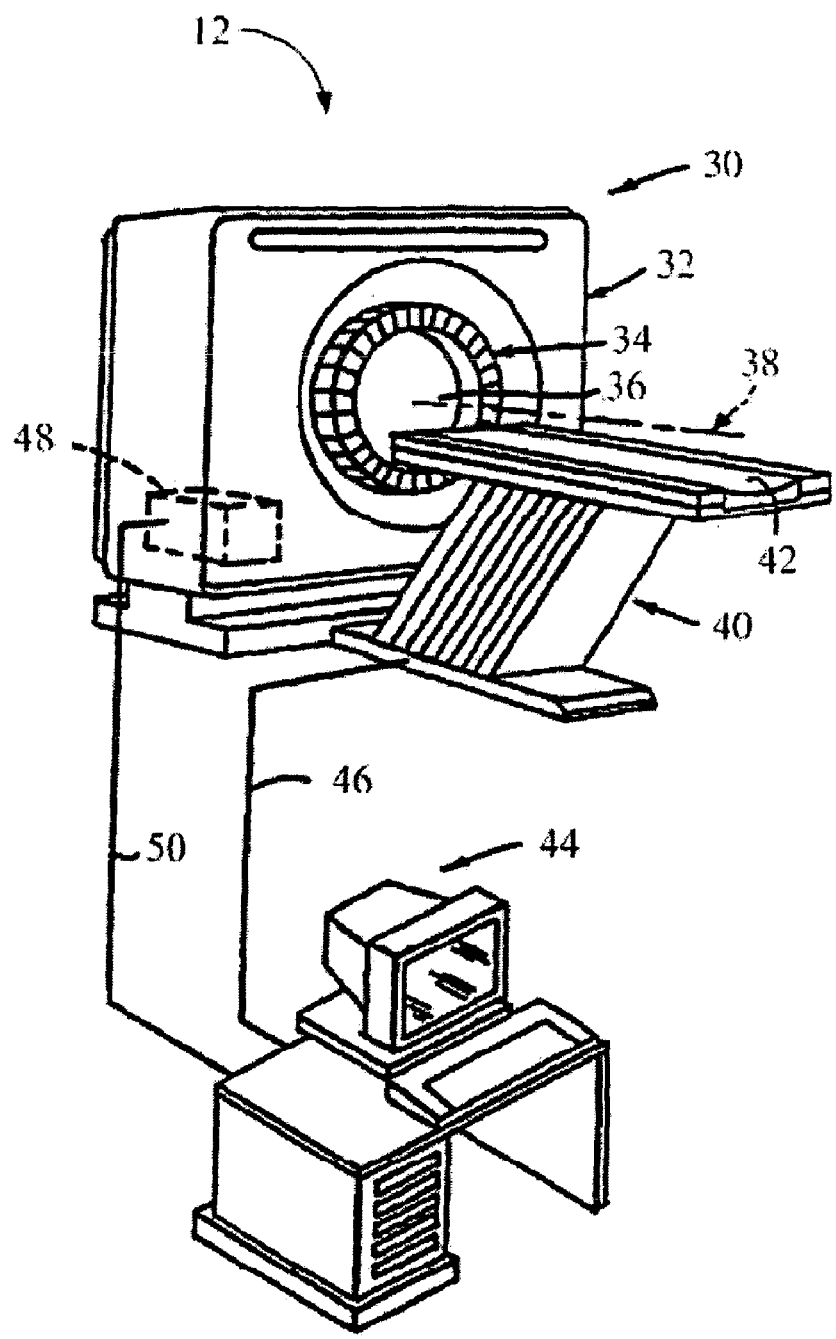
FIG. 10 is an isometric view of an embodiment of a PET imaging system that is used to generate PET sinograms and images.

FIG. 10 shows an embodiment of PET imaging system 12 that scans an object (not shown) to generate a PET emission image and a PET transmission image. PET imaging system 12 includes a PET scanner 30. PET scanner 30 includes a gantry 32 which supports a detector ring assembly 34 about a central opening, or bore 36. Detector ring assembly 34 is circular in shape, and is made up of multiple detector rings (not shown) that are spaced along a central axis 38 to form a cylindrical detector ring assembly. A table 40 is positioned in front of gantry 32 and is aligned with central axis 38 of detector ring assembly 34. A table controller (not shown) moves a table cradle 42 into bore 36 in response to commands received from an operator work station 44 through a communications link 46. A gantry controller 48 is mounted within gantry 32 and is responsive to commands received from operator work station 44 through a second communication link 50 to operate gantry 32.

Figure 11:
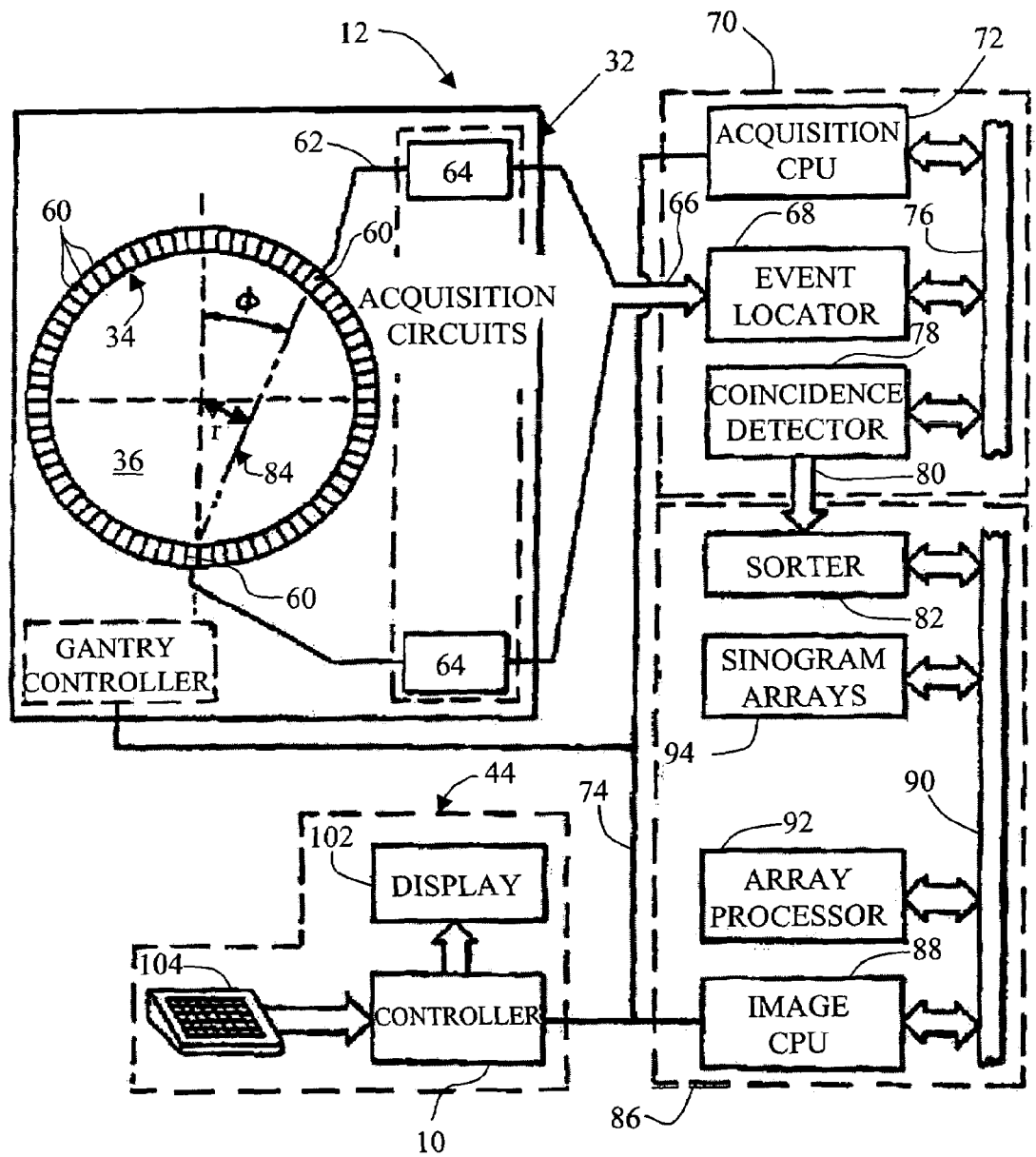
FIG. 11 is a block diagram of the PET imaging system of FIG. 10.

FIG. 11 shows a block diagram of PET imaging system 12 of FIG. 10. Each detector ring of detector ring assembly 34 includes detectors 60. Each detector 60 includes scintillator crystals (not shown). Each scintillator crystal is disposed in front of a photomultiplier tube (PMT) (not shown). PMTs produce analog signals on line 62 when a scintillation event occurs at one of the scintillator crystals that are disposed in front of the PMTs. The scintillation event occurs when a photon is received by one of the scintillator crystals. In one embodiment, photons are generated by administering a compound, such as, $^{11}$C-labeled glucose, $^{18}$F-labeled glucose, $^{13}$N-labeled ammonia and $^{15}$O-labeled water within the object, an emission of positrons by the compounds, a collision of the positrons with free electrons of the object, and generation of simultaneous pairs of photons. Alternatively, the photons can be emanate from rotating rod sources within a FOV of PET imaging system 12 for the purpose of object attenuation measurement. A set of acquisition circuits 64 is mounted within gantry 32 to receive the signals and produce digital signals indicating event coordinates (x,y) and total energy. These are sent through a cable 66 to an event locator circuit 68 housed in a separate cabinet. Each acquisition circuit 64 also produces an event detection pulse (EDP) which indicates the exact moment the scintillation event took place.

Event locator circuits 68 form part of a data acquisition processor 70 which periodically samples the signals produced by acquisition circuits 64. Processor 70 has an acquisition central processing unit (CPU) 72 which controls communications on a local area network 74 and a backplane bus 76. Event locator circuits 68 assemble the information regarding each valid event into a set of digital numbers that indicate precisely when the event took place and the position of a scintillation crystal which detected the event. This event data packet is conveyed to a coincidence detector 78 which is also part of data acquisition processor 70. Coincidence detector 78 accepts the event data packets from event locators 68 and determines if any two of them are in coincidence. Events which cannot be paired are discarded, but coincident event pairs are located and recorded as a coincidence data packet that is conveyed through a communication link 80 to a sorter 82.

Each pair of event data packets that is identified by coincidence detector 78 is described in a projection plane format using four variables r, v, θ, and Φ. Variables r and Φ identify a plane 84 that is parallel to central axis 38, with Φ specifying the angular direction of the plane with respect to a reference plane and r specifying the distance of the central axis from the plane as measured perpendicular to the plane. Variables v and θ (not shown) further identify a particular line within plane 84, with θ specifying the angular direction of the line within the plane, relative to a reference line within the plane, and v specifying the distance of center from the line as measured perpendicular to the line.

Sorter 82 forms part of an image reconstruction processor 86. Sorter 82 counts all events occurring along each projection ray, and stores that information in the projection plane format. Image reconstruction processor 86 also includes an image CPU 88 that controls a backplane bus 90 and links it to local area network 74. An array processor 92 also connects to backplane bus 90. Array processor 92 converts the event information stored by sorter 82 into a two dimensional sinogram array 94. Array processor 92 converts data, such as, for instance, PET emission data that is obtained by emission of positrons by the compound or transmission data that is obtained by transmission of photons by the rotating rod sources, from the projection plane format into the two-dimensional sinogram format. Examples of the 2D sinogram include a PET emission sinogram that is produced from PET emission data and a PET transmission sinogram that is produced from transmission data. Upon conversion of the data into the two-dimensional sinogram format, images can be constructed. Examples of the images include a PET emission image that is generated from the PET emission sinogram and a PET transmission image that is generated from the PET transmission sinogram. Operator work station 44 includes controller 10, a cathode ray tube (CRT) display 102, and a keyboard 104. Controller 10 connects to local area network 74 and scans keyboard 104 for input information. Through keyboard 104 and associated control panel switches, the operator controls calibration of PET imaging system 12, its configuration, and positioning of table 42 for a PET scan. Similarly, once Controller 10 receives a PET emission sinogram, a PET transmission sinogram, a PET transmission image or the PET emission image, the operator controls display of the sinograms or the images on CRT display 102 and performs a method for correcting the PET emission image.

Figure 12:
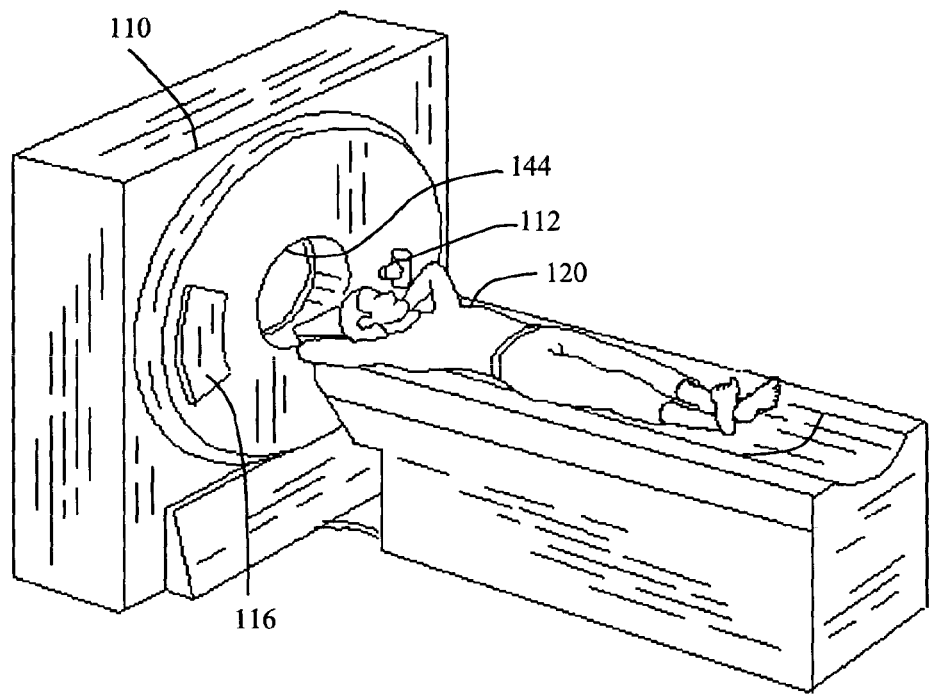
FIG. 12 is an embodiment of a computed tomography (CT) scanner of a CT imaging system that is used to generate CT sinograms and CT images.
Figure 13:
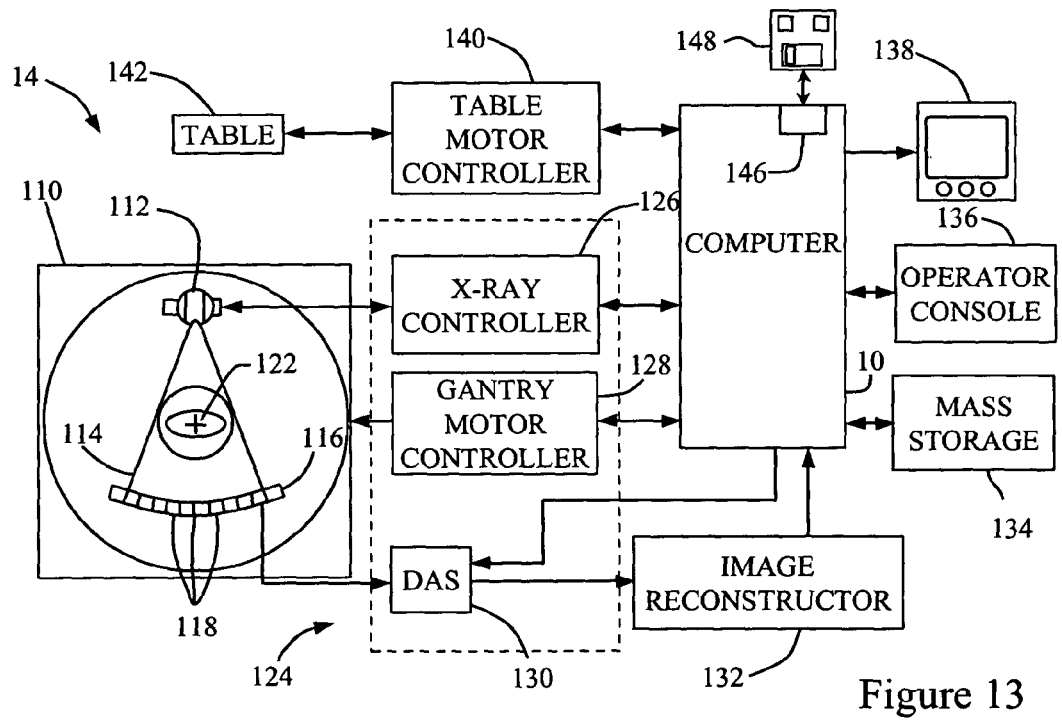
FIG. 13 is a block diagram of the CT imaging system of FIG. 12.

FIG. 12 shows an embodiment of a CT scanner of CT imaging system 14 and FIG. 13 shows a block diagram of CT imaging system 14. CT imaging system 14 includes a gantry 110. Gantry 110 has an x-ray radiation source 112 that projects a beam of x-ray radiation 114 toward a detector array 116 on the opposite side of gantry 110. Detector array 116 is formed by detector elements 118 that together sense the projected x-rays that pass through an object 120, for example a medical patient or a phantom. Each detector element 118 produces an electrical signal that represents the intensity of an impinging x-ray beam and hence the attenuation of the beam as it passes through object 120. During a scan to acquire CT data, gantry 110 and the components mounted thereon rotate about a center of rotation 122. Detector array 116 is fabricated in a multi-slice configuration such that detector array 18 has a plurality of rows of detector elements 118. During a twin beam helical scan, the CT data is acquired from two detector rows at the same time. One or more additional rows of detector elements 118 in such configurations are arranged parallel to illustrated row 116, and each row is transverse to the translation direction of object 120.

Rotation of gantry 110 and the operation of x-ray source 112 are governed by a control mechanism 124 of CT system 14. Control mechanism 124 includes an x-ray controller 126 that provides power and timing signals to x-ray source 112 and a gantry motor controller 128 that controls the rotational speed and position of gantry 110. A data acquisition system (DAS) 130 in control mechanism 124 samples analog data from detector elements 118 and converts the analog data to digital signals for subsequent processing. An image reconstructor 132 receives sampled and digitized x-ray data from DAS 130 and performs high-speed image reconstruction. The CT data is stored in a storage device 134. The reconstructed CT image is applied as an input to controller 10 which stores the CT image in storage device 134. In an alternative embodiment, a CT sinogram is generated from the CT data. The CT sinogram is a histogram that provides information of a number of photons that are detected by a scintillation crystal (not shown) of each detector element 118. Controller 10 also receives commands and scanning parameters from an operator via console 136 that has a keyboard (not shown). An associated display 138, such as a cathode ray tube or a liquid crystal display, allows the operator to observe the reconstructed image and the CT sinogram from controller 10. The operator supplied commands and parameters are used by controller 10 to provide control signals and information to DAS 130, x-ray controller 126 and gantry motor controller 128. In addition, controller 10 operates a table motor controller 140 which controls a motorized table 142 to position object 120 in gantry 110. Particularly, table 142 moves portions of object 120 through gantry opening 144.

In one embodiment, controller 10 includes a device 146 for reading and writing onto removable media 148. For example, device 146 is a floppy disk drive, a compact disc read/write (CD-R/W) drive, or a digital video device (DVD) drive. Correspondingly, media 148 is either a floppy disk, a compact disk, or a DVD. Device 146 and media 148 are used in one embodiment to transfer acquired CT data from CT imaging system 14 to another computer for further processing, or in another embodiment to input machine readable instructions that are processed by controller 10.

Controller 10 receives the CT image from image reconstructor 132 and executes a method for correcting a PET emission image. The method includes obtaining, from image CPU 88, a PET emission sinogram that is not corrected for attenuation, determining a boundary of portion of object 120 that is missing due to a FOV of CT imaging system 14 that is smaller than object 120, filling the portion with CT data that is based on CT data near the boundary, generating ACFs from CT data within the boundary and from CT data outside the boundary, correcting, with the ACFs, for attenuation in PET emission data, and reconstructing a corrected PET emission image from the corrected PET emission data.

Figure 14:
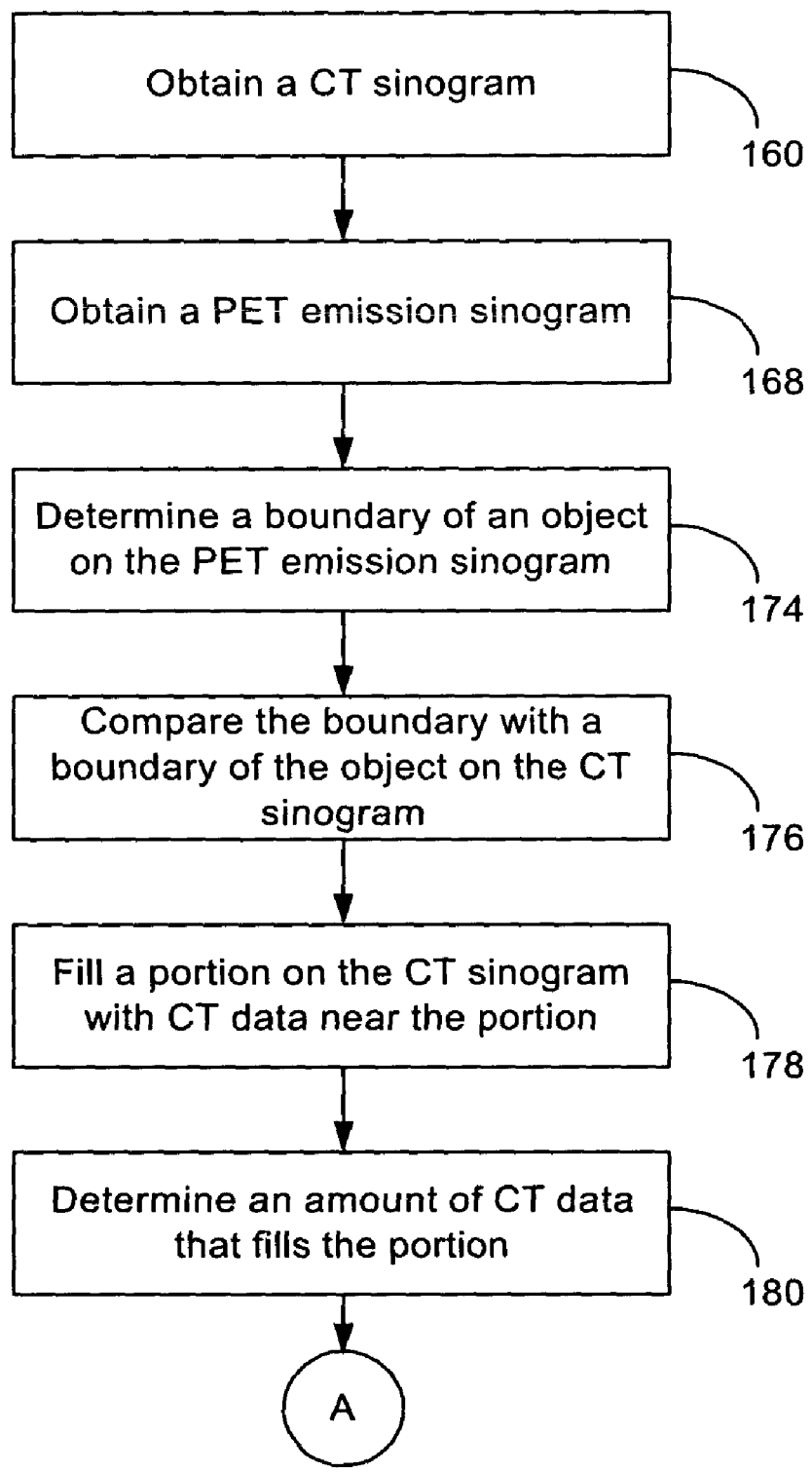
FIGS. 14 and 15 are flowcharts of an embodiment of a method for correcting a PET emission image for attenuation.
Figure 15:
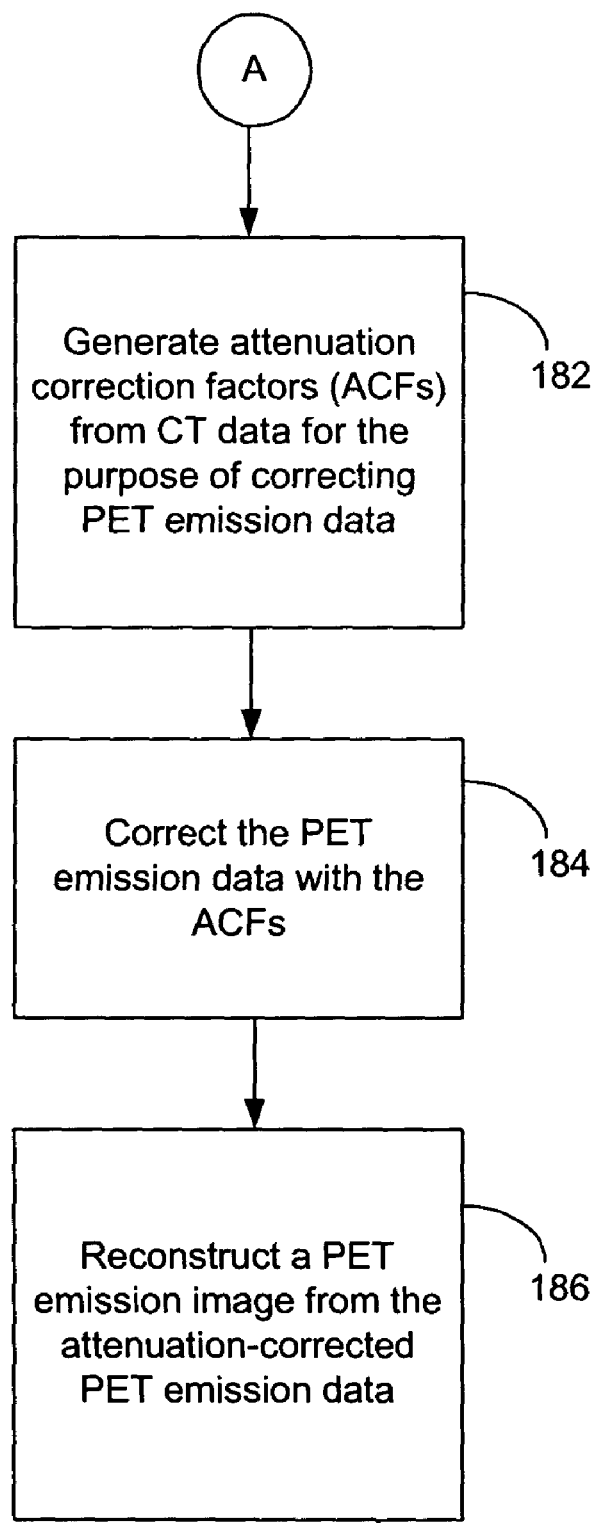
Figure 16:
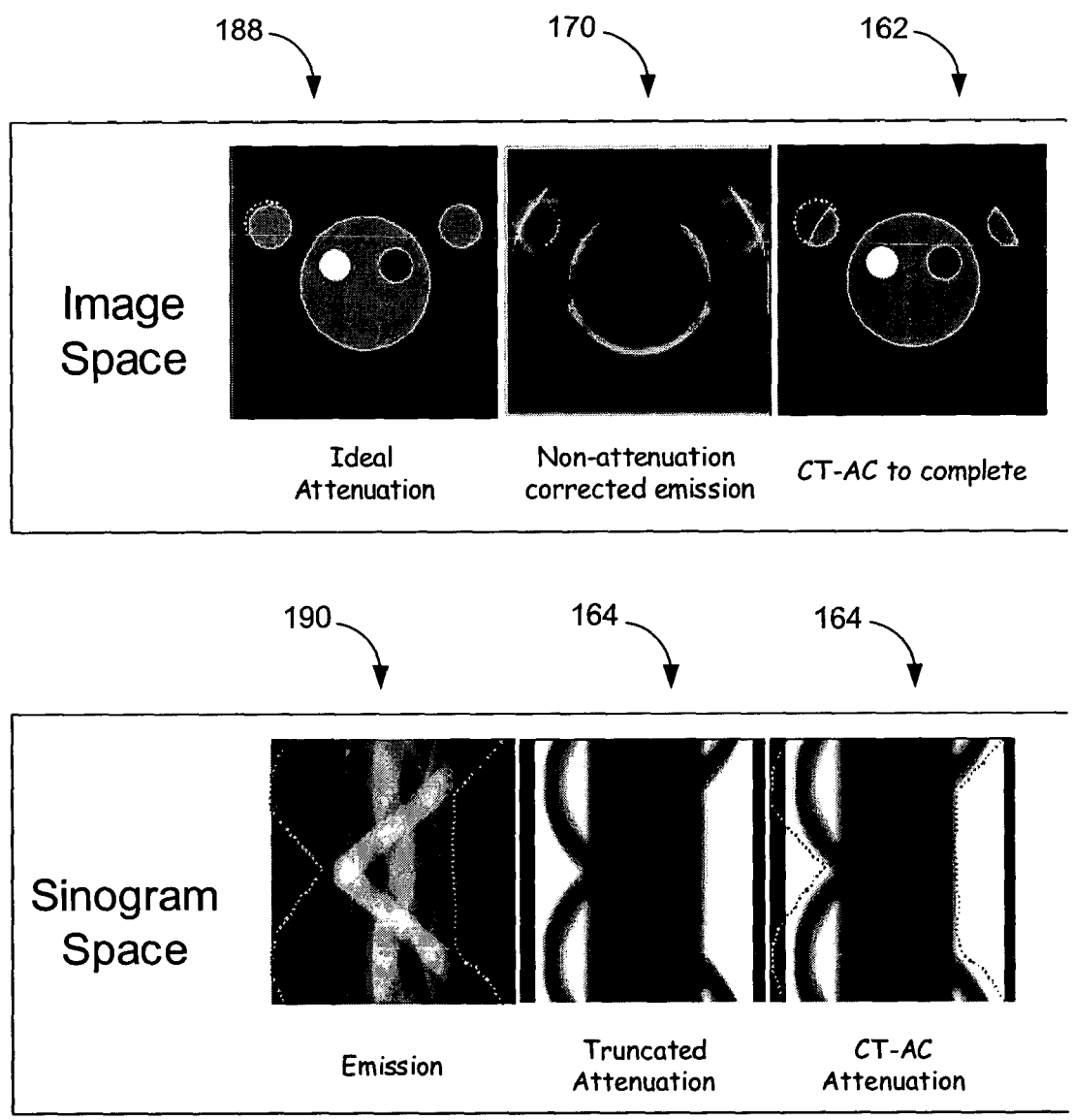
FIG. 16 shows a set of images and sinograms that are obtained by executing the method of FIGS. 14 and 15.
Figure 17:
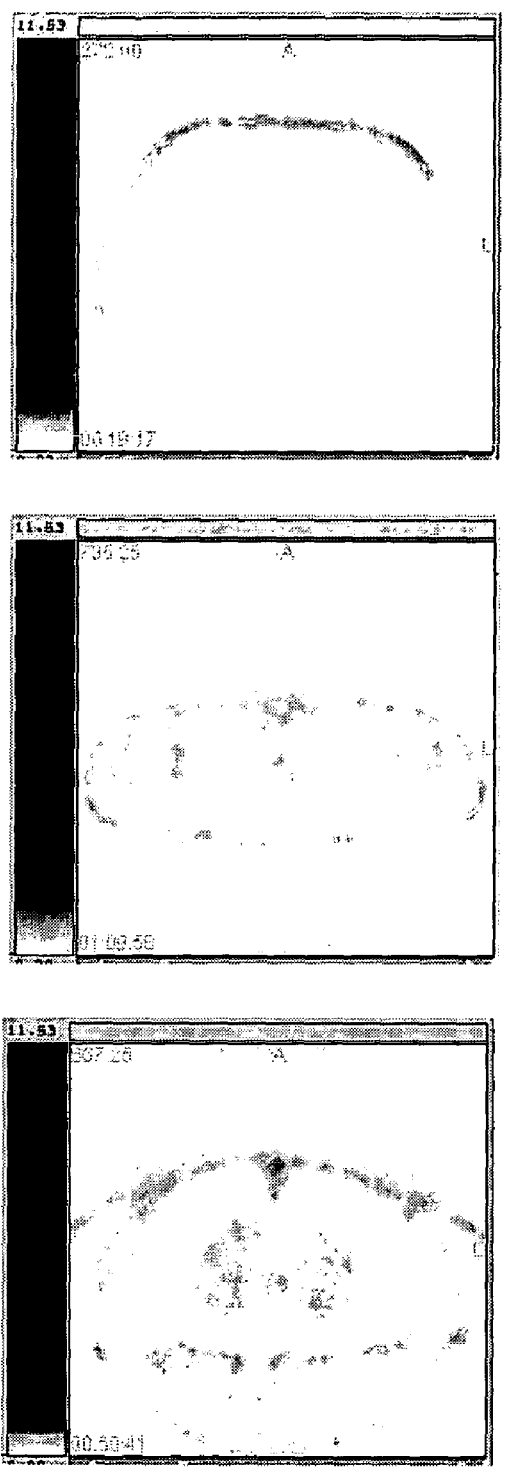
FIG. 17 shows PET emission images that are obtained by using the PET imaging system of FIG. 11.
Figure 18:
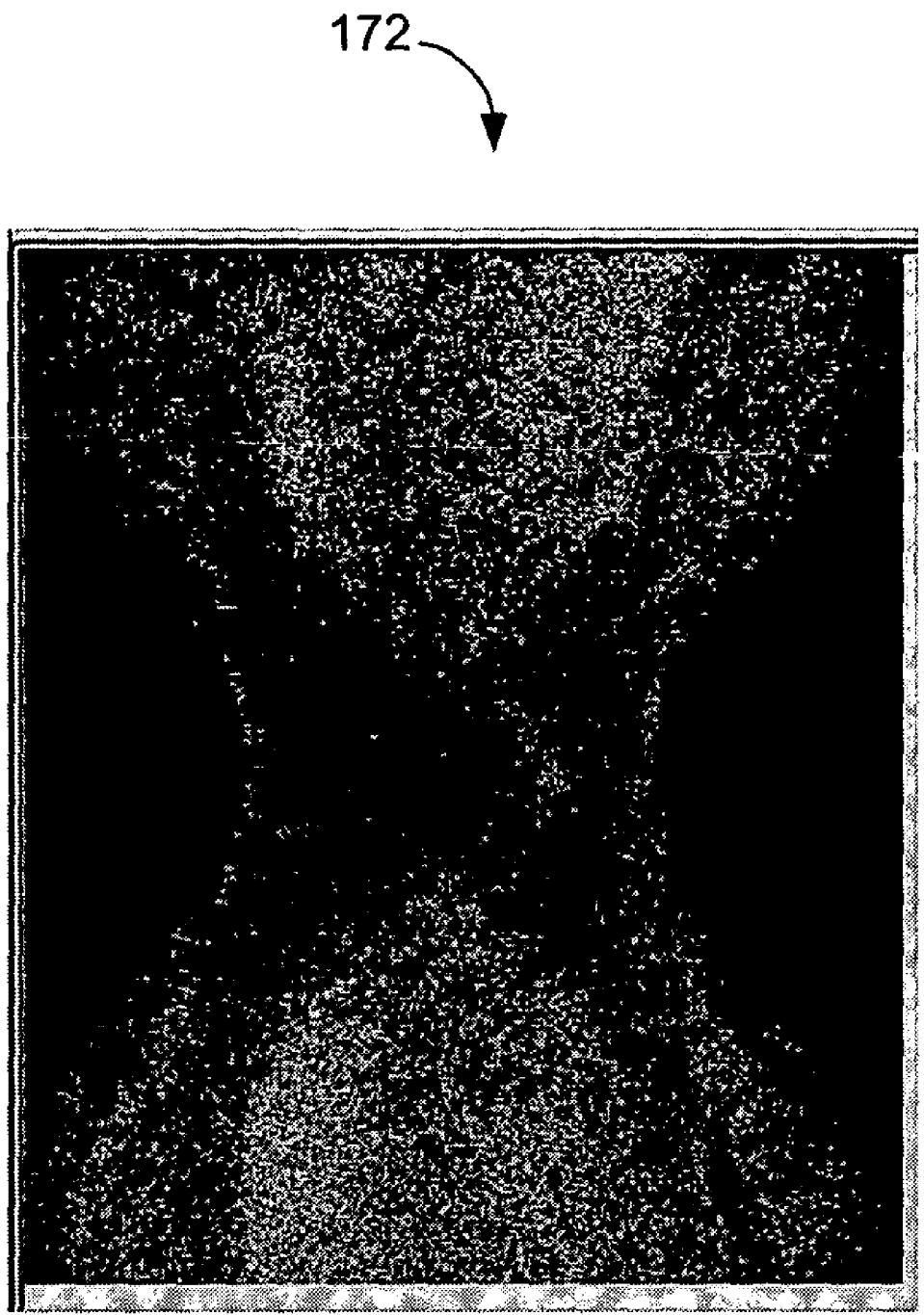
FIG. 18 shows a PET emission sinogram that is created by operating the PET imaging system of FIG. 11.

FIGS. 14 and 15 are flowcharts of an embodiment of a method for correcting a PET emission image. The method is executed by controller 10. The method includes obtaining a CT image 162, which is shown in FIG. 16, from image reconstructor 132 that constructs CT image 162 from CT data acquired by a CT scan. The method further includes a step 160 of obtaining a CT ACF sinogram 164 from controller 10. CT ACF sinogram 164 is generated by reprojection of CT image 162 and converting it to ACFs. CT image 162 does not include a portion of object 120 because the portion lies outside the FOV of CT imaging system 14. The portion is shown as a black area that is highlighted by dotted lines and surrounded by a grey area on a small circle on CT image 162. An example of FOVs of CT imaging system 14 includes a diameter of less than 60 cm. Another example of FOV of CT imaging system 14 includes a diameter of 50 cm. The method further includes a step 168 of obtaining a PET emission sinogram 190 of object 120 without correction of attenuation in PET emission data from which PET emission image 170 is constructed. Examples of three non-attenuation-corrected PET emission images with different patients within a FOV of 55 cm are shown in FIG. 17. The PET emission data is acquired from object 120 that fits within a FOV of PET imaging system 12. An example of the FOV of PET imaging system 12 includes a diameter between 60 cm and 70 cm. Histogramming the PET emission data generates a PET emission sinogram 172, which is shown in FIG. 18. The method also includes a step 174 of determining a boundary of object 120 on PET emission sinogram 190. The boundary is determined by traversing radially inward from an edge of the PET emission sinogram 190, determining whether an intensity of a pixel along the traversed path is above a threshold, and designating the pixel as an element of the boundary if the pixel is above the threshold. The thresholding routine can be made "smart" by using consistency conditions, such as only allowing a change by 1-2 pixels in location as a function of moving down PET emission sinogram 190 (see dashed lines). Further, the data could be smoothed prior to execution of the algorithm and the entire process can be made iterative. Knowledge of the non-truncated portions of the CT ACF sinogram (164) could be used to aid or initiate this routine. Examples of the threshold include using a fraction of the highest number of counts found along a row of pixels of PET emission sinogram 190, such as 0.2*max. The method continues with a step 176 that compares the boundary to a boundary of object 120 on CT sinogram 164. Such a comparison is illustrated by dotted lines on CT sinogram 164. The boundary on CT sinogram 164 is determined in a similar manner as the boundary on PET emission sinogram 190 is determined, which is described above.

The method includes a step 178 of filling the portion on CT image 162 or CT sinogram 164 with CT data that is near the truncated portion on CT image 162. For example, the portion is filled with the average CT data value that is inside the grey area of the small circle on left corner of CT image 162. In an alternative embodiment, the portion is filled with CT data, such as an average tissue value, that is independent of CT data lying within the grey portion of the small circle on the left corner of CT image 162 and lying outside the radius of the small circle. In yet another alternative embodiment, the portion is filled with CT data that is equal to a value of CT data that lies with the grey portion of the small circle on the left corner of CT image 162. In still another alternative embodiment, an average of CT data that lies within the grey portion of the small circle on the left corner of CT image 162 can be used to fill the portion that is black and that lies within the small circle on CT image 162. In yet another alternative embodiment, the method includes filling the portion on CT image 162 with CT data that lies near the portion on CT image 162, and does not create artifacts on a CT image. The method further includes a step 180 of determining an amount of CT data that fills the black portion of the small left circle on CT image 162. The accuracy of determination of the boundary is based on noise characteristics of the PET emission data and whether all elements of the boundary of object 120 on PET emission sinogram 190 have been determined.

Figure 19:
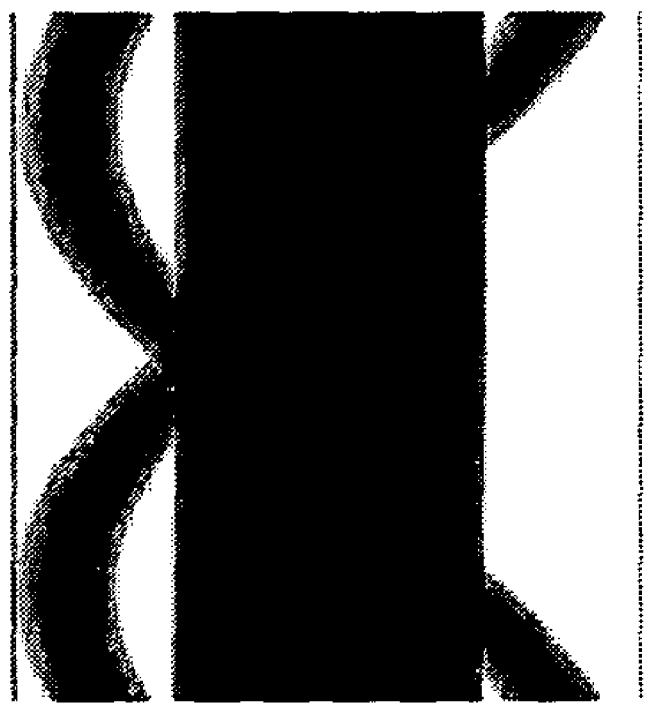
FIG. 19 shows a complete attenuation correction factor (ACF) sinogram that is created by executing the method of FIGS. 14 and 15.

The method further includes a step 182 of generating ACFs from of the corrected ("completed") CT image data, including CT data of the small left circle within CT image 162. This is the process of "reprojecting" the complete image to form a complete ACF sinogram 194, which is shown in FIG. 19. The method continues with a step 184 of correcting the PET emission data that is not corrected for attenuation with the ACFs of ACF sinogram 194. The method includes a step 186 of constructing PET emission image 188 from the corrected PET emission data. Histogramming the corrected PET emission data produces a PET emission sinogram from which a PET emission image can be reconstructed.

An alternative embodiment of the method includes obtaining PET emission sinogram 172, which is a histogram of the PET emission data that is not corrected for attenuation and obtaining CT sinogram 164. The method further includes determining a boundary of the object 120 on PET emission sinogram 172. The boundary is determined by traversing a first row of pixels in PET emission sinogram 172, searching for a pixel having a maximum intensity value along the traversed path, referred to as a maximum intensity pixel, searching for a first pixel having an intensity value above a percentage of the maximum intensity value while traversing the first row in one direction, such as, for instance, from left to right, searching for a second pixel having an intensity value that is above the percentage while traversing the first row in an opposite direction, such as, for instance, from right to left, calculating a mean intensity value from the intensity values of the first and second pixels, and traversing the remaining rows of PET emission sinogram 172 to find pixels with a threshold value that is greater than a percentage of the mean intensity value. Examples of the percentage of the maximum intensity value include 10% to 20% of the maximum intensity value and examples of percentage of the mean intensity value include 10% to 20% of the mean intensity value. Each of the remaining rows are traversed in one direction to find a pixel having an intensity value above the percentage of the mean intensity value and are traversed in an opposite direction to find a pixel having an intensity value that is above the percentage of the mean intensity value. A continuity constraint would be placed on the algorithm such that the object boundary is forced to be continuous.

The method includes comparing the boundary of object 120 on PET emission sinogram 172 with a boundary of object 120 on CT sinogram 164 and filling a portion between the boundaries in a similar manner as described above. The boundary of object 120 on CT sinogram 164 is determined in a similar manner as the boundary of object 120 on PET emission sinogram 172 is determined. The method continues by generating ACFs from CT data within a portion 192 of object 120. The method also includes correcting the PET emission data with ACFs and generating corrected PET emission sinogram 190 in a manner described above.

Hence, the systems and methods described herein generate attenuation-corrected PET emission images by filling CT data truncated out of CT image 162. The systems and methods use PET emission sinogram 190 that is not corrected for attenuation to obtain the black portion of small left circle of CT image 162 that is filled with the CT data.

While the invention has been described in terms of various specific embodiments, those skilled in the art will recognize that the invention can be practiced with modification within the spirit and scope of the claims.

What is claimed is:

1. A method for correcting a positron emission tomography (PET) emission image comprising:
    obtaining a PET emission sinogram of an object;
    obtaining a computed tomography (CT) image for a scanned portion of the object, the object having a truncated portion outside a field of view (FOV) of a CT image;
    obtaining a CT sinogram for the scanned portion of the object;
    determining a correction set of CT data based on a measured set of CT data within the CT sinogram;
    generating modified attenuation correction factors from the measured and correction sets of CT data; and
    correcting the PET sinogram using the modified attenuation correction factors.

2. A method in accordance with claim 1 further comprising:
    determining a boundary of the object on the PET sinogram; and
    comparing the boundary on the PET sinogram with a boundary of the object on the CT sinogram to determine the truncated portion.

3. A method in accordance with claim 2 wherein determining the boundary of the object on the PET sinogram comprises:
    traversing radially outward from a center of the PET sinogram;
    determining whether an intensity of a pixel along the traversed path is above a threshold; and
    designating the pixel as a portion of the boundary of the object on the PET sinogram if the intensity of the pixel is above the threshold.

4. A method in accordance with claim 2 wherein determining the boundary of the object on the PET sinogram comprises:
    traversing radially inward toward a center of the PET sinogram;
    determining whether an intensity of a pixel along the traversed path is above a threshold; and
    designating the pixel as a portion of the boundary of the object on the PET sinogram if the intensity of the pixel is above the threshold.

5. A method in accordance with claim 1 wherein the correction set of CT data is a subset of the measured CT data forming the CT sinogram.

6. A method in accordance with claim 1 wherein data values within the correction set are equal to a data value in the measured set of CT data.

7. A method in accordance with claim 1 further comprising:
    determining a boundary of the object on the PET sinogram, the PET sinogram representing PET emission data used to construct a PET image; and
    comparing the boundary of the object on the PET sinogram with a boundary of the object on the CT sinogram having the measured CT data that is used to construct the CT image.

8. A method in accordance with claim 1 further comprising:
    determining a boundary of the object on the PET sinogram, the PET sinogram representing PET emission data used to construct a PET image, wherein determining the boundary of the object on the PET sinogram comprises:
    traversing a first row of pixels in the PET sinogram;
    finding a first pixel having a maximum intensity value along the traversed path;
    finding a second pixel having an intensity value that is above a percentage of the maximum intensity value;
    traversing in one direction the first row of pixels;
    finding a third pixel having an intensity value that is above the percentage;
    calculating a mean intensity value from the intensity values of the second and third pixels; and
    traversing the remaining rows of pixels in the PET sinogram to find pixels with a threshold value that is greater than a percentage of the mean value; and comparing the boundary of the object on the PET sinogram with a boundary of the object on the CT sinogram having the measured CT data that is used to construct the CT image.

9. A method in accordance with claim 1 further comprising:
determining an amount of the CT data in the correction set based on a boundary of the object on the PET sinogram and whether all elements of a boundary of the object on a PET image from which the PET sinogram is generated are determined.

10. A method in accordance with claim 1 wherein determining the correction set of CT data based on the measured set of CT data within the CT sinogram comprises determining the correction set of CT data based on the measured set of CT data within the CT sinogram, the measured set of CT data being located proximate a boundary of the object on the CT sinogram, being independent of measured CT data remote from the boundary, and does not produce artifacts.

11. A method in accordance with claim 1 wherein determining the correction set of CT data based on the measured set of CT data within the CT sinogram comprises determining the correction set of CT data in which each datum is equal to a datum of the measured set of CT data.

12. A computer-readable medium encoded with a program configured to:
obtain a PET emission sinogram of an object;
obtain a computed tomography (CT) image for a scanned portion of the object, the object having a truncated portion outside a field of view (FOV) of a CT image;
obtain a CT sinogram for the scanned portion of the object;
determine a correction set of CT data based on a measured set of CT data within the CT sinogram;
generate modified attenuation correction factors from the measured and correction sets of CT data; and
correct the PET sinogram using the modified attenuation correction factors.

13. A computer-readable medium in accordance with claim 12 wherein the program is further configured to:
determine a boundary of the object on the PET sinogram; and
compare the boundary on the PET sinogram with a boundary of the object on the CT sinogram to determine the truncated portion.

14. A computer-readable medium in accordance with claim 12 wherein to determine the boundary of the object on the PET sinogram the program configured to
traverse radially outward from a center of the PET sinogram;
determine whether an intensity of a pixel along the traversed path is above a threshold; and
designate the pixel as a portion of the boundary of the object on the PET sinogram if the intensity of the pixel is above the threshold.

15. A computer-readable medium in accordance with claim 12 wherein the correction set of CT data is a subset of the measured CT data forming the CT image.

16. A computer-readable medium in accordance with claim 12 wherein data values within the correction set are equal to a data value in the measured set of CT data.

17. A computer-readable medium in accordance with claim 12 wherein the program is further configured to:
determine a boundary of the object on the PET sinogram, the PET sinogram representing PET emission data used to construct a PET image; and
compare the boundary of the object on the PET sinogram with a boundary of the object on the CT sinogram having the measured CT data that is used to construct the CT image.

18. A computer-readable medium in accordance with claim 12 wherein the program is further configured to:
determine a boundary of the object on the PET sinogram, the PET sinogram representing PET emission data used to construct a PET image, wherein determining the boundary of the object on the PET sinogram comprises:
traverse a first row of pixels in the PET sinogram;
find a first pixel having a maximum intensity value along the traversed path;
find a second pixel having an intensity value that is above a percentage of the maximum intensity value;
traverse in one direction the first row of pixels;
find a third pixel having an intensity value that is above the percentage;
calculate a mean intensity value from the intensity values of the second and third pixels; and
traverse the remaining rows of pixels in the PET sinogram to find pixels with a threshold value that is greater than a percentage of the mean value; and
compare the boundary of the object on the PET sinogram with a boundary of the object on the CT sinogram having the measured CT data that is used to construct the CT image.

19. A computer-readable medium in accordance with claim 12 wherein the program is further configured to:
determine an amount of the CT data in the correction set based on a boundary of the object on the PET sinogram and whether all elements of a boundary of the object on a PET image from which the PET sinogram is generated are determined.

20. A computer readable medium in accordance with claim 12 wherein to determine the correction set of CT data based on the measured set of CT data within the CT sinogram the program configured to determine the correction set of CT data in which each datum is equal to a datum of the measured set of CT data.

21. A computer-readable medium in accordance with claim 12 wherein to determine the correction set of CT data based on the measured set of CT data within the CT image, the program configured to determine the correction set of CT data based on the measured set of CT data within the CT image, the measured set of CT data being located proximate the boundary, being independent of measured CT data remote from the boundary, and producing no artifacts.

22. A method for correcting a positron emission tomography (PET) emission image comprising:
obtaining a computed tomography (CT) sinogram that is missing a portion of an object;
creating a non-attenuation-corrected PET emission sinogram of the object, the PET emission sinogram being a histogram of PET emission data;
determining a boundary of the object on the PET emission sinogram;
comparing the boundary with a boundary of the object on the CT sinogram to determine the truncated portion;
filling the portion with a first set of CT data located close to a portion of the boundary of the object on the CT sinogram;
generating attenuation correction factors from the first set and a second set of CT data located outside the portion; and
correcting the PET emission data using the attenuation correction factors.

23. A method in accordance with claim 22 wherein determining the boundary of the object on the PET emission sinogram comprises:

traversing radially inward from an edge of the PET emission sinogram;
determining whether an intensity of a pixel along the traversed path is above a threshold; and
designating the pixel as a portion of the boundary if the intensity of the pixel is above the threshold.

24. An imaging system for correcting a positron emission tomography (PET) emission image comprising:

a scanner having a plurality of detectors for acquiring a measured set of CT data;
a controller operationally coupled to the scanner, the controller configured to:
obtain a PET emission sinogram of an object;
obtain a computed tomography (CT) image for a scanned portion of the object, the object having a truncated portion outside a field of view (FOV) of a CT image;
obtain a CT sinogram for the scanned portion of the object;
determine a correction set of CT data based on a measured set of CT data within the CT sinogram;
generate modified attenuation correction factors from the measured and correction sets of CT data; and
correct the PET sinogram using the modified attenuation correction factors.

25. An imaging system for correcting an image comprising:

a scanner having a plurality of detectors for acquiring a first dataset and a second dataset, the first dataset acquired from a first modality and the second dataset of data acquired from a second modality;
a controller operationally coupled to the scanner, the controller configured to:
obtain the first dataset of an object using the first modality;
obtain the second dataset for a scanned portion of the object, the object having a truncated portion outside a field of view (FOV) of the second modality;
obtain a sinogram that includes the second data set;
determine a correction dataset based on the second dataset within the sinogram, the second dataset being located proximate a boundary of the object on the second modality and being independent of data in the second dataset that is remote from the boundary;
generate attenuation correction factors from the second and correction datasets; and
correct the first dataset using the attenuation correction factors.

* * * * *